United States Patent [19]

Takahashi et al.

[11] Patent Number: 4,666,938
[45] Date of Patent: May 19, 1987

[54] FUNGICIDAL ANILINE DERIVATIVES

[75] Inventors: Junya Takahashi; Toshiro Kato, both of Hyogo; Hiroshi Noguchi, Osaka; Yukio Oguri, Osaka; Shigeo Yamamoto, Osaka; Katsuzo Kamoshita, Osaka, all of Japan

[73] Assignee: Sumitomo Chemical Company, Limited, Osaka, Japan

[21] Appl. No.: 613,773

[22] Filed: May 24, 1984

[30] Foreign Application Priority Data

Jun. 6, 1983 [GB] United Kingdom ............... 8315495

[51] Int. Cl.$^4$ .................. A01N 47/20; C07C 125/065
[52] U.S. Cl. ................................. 514/479; 514/485; 560/24; 560/29
[58] Field of Search ..................... 560/29, 30, 24; 424/300; 514/485, 479

[56] References Cited

FOREIGN PATENT DOCUMENTS 0063905 11/1982 European Pat. Off. .

Primary Examiner—Dolph H. Torrence
Attorney, Agent, or Firm—Birch, Stewart, Kolasch & Birch

[57] ABSTRACT

A compound of the formula:

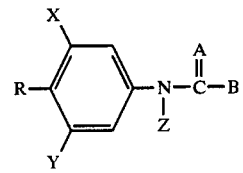

useful as a fungicidal agent against phytopathogenic fungi, particularly their strains resistant to benzimidazole and thiophanate fungicides and/or cyclic imide fungicides.

8 Claims, No Drawings

FUNGICIDAL ANILINE DERIVATIVES

This invention relates to fungicidal aniline derivatives.

Benzimidazole and thiophanate fungicides such as Benomyl (methyl 1-(butylcarbamoyl)benzimidazol-2-ylcarbamate), Fubelidazol (2-(2-furyl)benzimidazole), Thiabendazole (2-(4-thiazolyl)benzimidazole), Carbendazim (methyl benzimidazol-2-ylcarbamate), Thiophanate-methyl (1,2-bis(3-methoxycarbonyl-2-thioureido)-benzene), Thiophanate (1,2-bis(3-ethoxycarbonyl-2-thioureido)benzene), 2-(O,S-dimethylphosphorylamino)-1-(3'-methoxycarbonyl-2'-thioureido)benzene and 2-(O,O-dimethylthiophosphorylamino)-1-(3'-methoxycarbonyl-2'-thioureido)benzene are known to exhibit an excellent fungicidal activity against various plant pathogenic fungi, and they have been widely used as agricultural fungicides since 1970. However, their continuous application over a long period of time allows phytopathogenic fungi to develop a tolerance to them, whereby their plant disease-preventive effect is substantially lowered. Further, the fungi which developed a tolerance to certain kinds of benzimidazole or thiophanate fungicides also exhibit considerable tolerance to some other kinds of benzimidazole or thiophanate fungicides. Thus, they are apt to develop cross-tolerance. Therefore, if any material decrease of their plant disease-preventive effect in certain fields is observed, their application to such fields has to be discontinued. But, it is often observed that the density of drug-resistant organisms is not decreased even long after the discontinuation of the application. Although other kinds of fungicides have to be employed in such a case, only few are so effective as benzimidazole or thiophanate fungicides in controlling various phytopathogenic fungi. Benzimidazole and thiophanate fungicides will be hereinafter referred to as "benzimidazole thiophanate fungicides".

Cyclic imide fungicides such as Procymidone (3-(3',5'-dichlorophenyl)-1,2-dimethylcyclopropane-1,2-dicarboximide), Iprodione (3-(3',5'-dichlorophenyl)-1-iospropylcarbamoylimidazolidine-2,4-dione), Vinchlozolin (3-(3',5'-(dichlorophenyl)-5-methyl-5-vinyloxazolidin-2,4-dione), ethyl (RS)-3-(3',5'-dichlorophenyl)-5-methyl-2,4-dioxooxazolidine-5-carboxylate, etc., which are effective against various plant diseases, particularly those caused by *Botrytis cinerea,* have the same defects as previously explained with respect to the benzimidazole thiophanate fungicides.

In C.R. Acd. Sc. Paris, t. 289, S'erie D, pages 691–693 (1979), it is described that such herbicides as Barban (4-chloro-2-butynyl N-(3-chloropheyl)carbamate), Chlorobufam (1-methyl-2-propynyl N-(3-chlorophenyl)carbamate), Chlorpham (isopropyl N-(3-chlorophenyl)carbamate) and Propham (isopropyl N-phenylcarbamate) exhibit a fungicidal activity against certain organisms tolerant to some benzimidazole thiophanate fungicides. However, their fungicidal activity against the drug-resistant fungi is not strong enough, and hence, practically they can not be used as fungicides.

As a result of the study seeking a new type of fungicide, it has now been found that aniline derivatives of the formula:

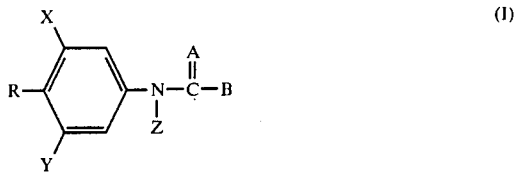

wherein X is a hydrogen atom, a halogen atom, a lower alkyl group, a lower alkoxy group or a nitro group; Y is a halogen atom, a lower alkyl group or a group of the formula: —OR$_1$, —CH$_2$OR$_1$, —COOR$_1$,

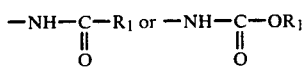

in which R$_1$ is a lower alkyl group; R is an iodine atom or a group of the formula: —R', —CH$_2$—A'—R',

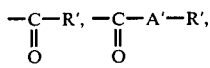

—CH=N—OR',

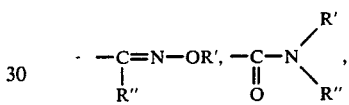

—N=CH—R', —NH—R',

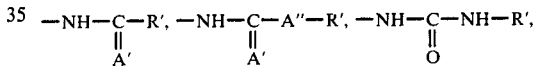

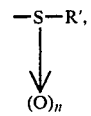

—SO$_2$—A'—R' or

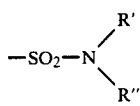

in which R' and R" are, same or different, each a cyclo(-lower)alkyl group, a lower alkyl group, a lower alkenyl group, a lower alkynyl group, a halo(lower)alkyl group, a lower alkoxy(lower)alkyl group, a cyano group, a cyano(lower)alkyl group or a hydrogen atom, A' and A" are, same or different, each an oxygen atom or a sulfur atom and n is 0, 1 or 2, with the proviso that R is not a hydrogen atom; Z is a hydrogen atom, a hydroxyl group, a lower alkyl group, a lower alkenyl group, a lower alkynyl group, a lower alkoxycarbonyl(-lower)alkyl group or a group of the formula:

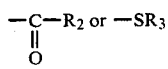

in which R$_2$ is a lower alkyl group, a lower cyclo(lower)alkyl group or a phenyl group and R$_3$ is a lower alkyl group, a phenyl group or a lower alkoxycarbonyl group; A is an oxygen atom or a sulfur atom; and B is a lower alkyl group, a lower alkenyl group, a cyclo(lower)alkyl group, a phenyl group or a group of the formula: —W—R₄ in which W is an oxygen atom or a sulfur atom and R₄ is a cyclo(lower)alkyl group, a lower alkyl group, a lower alkenyl group, a lower alkynyl group, a halo(lower)alkenyl group, a halo(lower)alkynyl group, a cyclo(lower)alkyl(lower)alkyl group, a phenyl group optionally substituted with halogen, or a lower alkyl group substituted with halogen, cyano, lower alkoxy, phenyl, lower alkenyloxy, halo(lower)akoxy, phenoxy and/or ar(lower)alkyloxy, exhibit an excellent fungicidal activity against plant pathogenic fungi which have developed resistance to benzimidazole thiophanate fungicides and/or cyclic imide fungicides. It is notable that their fungicidal potency against the organisms tolerant to benzimidazole thiophanate fungicides and/or cyclic imide fungicides (hereinafter referred to as "drug-resistant fungi" or "drug-resistant strains") is much higher than that against the organisms sensitive to benzimidazole thiophanate fungicides and/or cyclic imide fungicides (hereinafter referred to as "drug-sensitive fungi" or "drug-sensitive strains").

The term "lower" used hereinabove and hereinafter in connection with organic groups such as alkyl, alkenyl or alkynyl indicates to have not more than 12 carbon atoms. When the term "lower" is used for non-cyclic organic groups, it may preferably mean to have not more than 8 carbon atoms, particularly not more than 6 carbon atoms. When used for cyclic organic groups, it may preferably indicate to have 3 to 10 carbon atoms, especially 3 to 8 carbon atoms. Examples of the term "acyl" includes lower alkanoyl and benzoyl. The term "ar" is the abbreviation of "aryl" which includes phenyl substituted or not with lower alkyl.

The aniline derivatives of the formula (I) are fungicidally effective against a wide scope of plant pathogenic fungi, of which examples are as follows: *Podosphaera leucotricha, Venturia inaequalis, Mycosphaerella pomi, Marssonina mali* and *Sclerotinia mali* of apple, *Phyllactinia kakicola* and *Gloeosporium kaki* of persimmon, *Cladosporium carpophilum* and *Phomopsis* sp. of peach, *Cercospora viticola, Uncinula necator, Elsinoe ampelina* and *Glomerella cingulata* of grape, *Cercospora beticola* of sugarbeet, *Cercospora arachidicola* and *Cercospora personata* of peanut, *Erysiphe graminis* f. sp. *hordei, Cercosporella herpotrichoides* and *Fusarium nivale* of barley, *Erysiphe graminis* f. sp. *tritici* of wheat, *Sphaerotheca fuliginea* and *Cladosporium cucumerinum* of cucumber, *Cladosporium fulvum* of tomato, *Corynespora melongena* of eggplant, *Sphaerotheca humuli, Fusarium oxysporum* f. sp. *fragarie* of strawberry, *Botrytis alli* of onion, *Cercospora apii* of cerely, *Phaeoisariopsis griseola* of kidney bean, *Erysiphe cichloracearum* of tobacco, *Diplocarpon rosae* of rose, *Elsinoe fawcetti, Penicillium italicum, Penicillium digitatum* of orange, *Botrytis cinerea* of cucumber, eggplant, tomato, strawberry, pimiento, onion, lettuce, grape, orange, cyclamen, rose or hop, *Sclerotinia sclerotiorum* of cucumber, eggplant, pimiento, lettuce, celery, kidney bean, soybean, azuki bean, potato or sunflower, *Sclerotinia cinerea* of peach or cherry, *Mycosphaerella melonis* of cucumber or melon, etc. Namely, the aniline derivatives (I) are highly effective in controlling the drug-resistant strains of these fungi.

The aniline derivatives (I) are also fungicidally effective against fungi sensitive to known fungicides as well as fungi to which known fungicides are ineffective. Examples of such fungi are *Pyricularia oryzae, Pseudoperonospora cubensis, Plasmopara viticola, Phytophthora infestans*, etc.

Advantageously, the aniline derivatives (I) are low in toxicity and have little detrimental effects on mammals, fishes and so on. Also, they may be applied to the agricultural field without causing any material toxicity to important crop plants.

The aniline derivatives (I) can be prepared by either one of the following procedures:

Procedure (a):

The compound (I) can be prepared by reacting a compound of the formula:

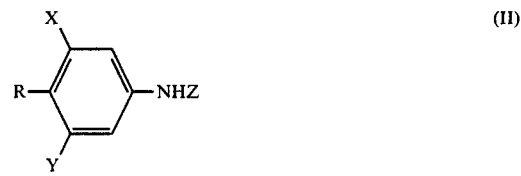

wherein X, Y, Z and R are each as defined above, with a compound of the formula:

wherein A and B are each as defined above and R₅ is a halogen atom or with a compound of the formula:

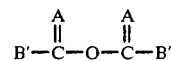

wherein A is as defined above and B' is a lower alkyl group, a lower alkenyl group, a cyclo(lower)alkyl group or a phenyl group.

The reaction is usually carried out in the presence of an inert solvent (e.g. benzene, toluene, tetrahydrofuran, chloroform, ethyl acetate, dimethylformamide). If desired, the reaction may be performed in the presence of a basic agent (e.g. triethylamine, sodium hydroxide, N,N-diethylaniline) so as to obtain the compound (I) in a high yield. The reaction may be accomplished at a temperature of 0° to 150° C. instantaneously or within 12 hours.

Procedure (b):

The compound of the formula (I) wherein Z is a hydrogen atom and b is a group of the formula: —W—R₄ in which W and R₄ are each as defined above can also be prepared by reacting a compound of the formula:

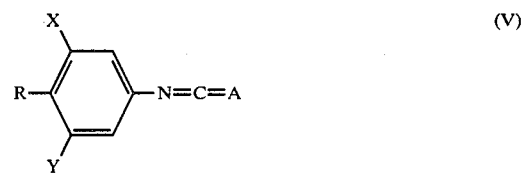

wherein X, Y, R and A are each as defined above with a compound of the formula:

wherein W and $R_4$ are each as defined above.

The reaction is usually carried out in the presence of an inert solvent (e.g. benzene, toluene, xylene, diethyl ether, tetrahydrofuran, dioxane, dimethylformamide, chloroform, carbon tetrachloride). If desired, the reaction may be performed in the presence of a catalyst (e.g. triethylamine, N,N-diethylaniline, 1,4-diazbicyclo[2.2.2]-octane) so as to obtain the compound (I) in a high yield. The reaction may be accomplished at a temperature of 0° to 50° C. instantaneously or within 10 hours.

The starting compound (V) can be prepared by reacting a compound of the formula:

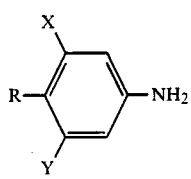
(VII)

wherein X, Y and R are each as defined above with phosgene or thiophosgene.

The reaction is usually carried out in the presence of an inert solvent (e.g. benzene, toluene, xylene, ethyl acetate). The reaction may be accomplished at a temperature of 50° C. to the boiling point of the solvent instantaneously or within 10 hours.

Procedure (c):

The compound of the formula (I) can also be prepared by reacting a compound of the formula:

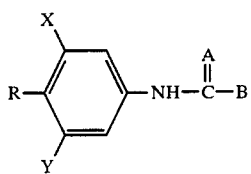
(VIII)

wherein X, Y, R, A and B are each as defined above with a compound of the formula:

 (IX)

Z—R6 wherein Z is as defined above and $R_6$ is a leaving group (e.g. tosyloxy, mesyloxy, halogen).

The reaction is usually carried out in the presence of an inert solvent (e.g. benzene, toluene, xylene, dioxane, chloroform). If desired, a base (e.g. triethylamine, sodium hydroxide, sodium hydride) may be present in the reaction system. The reaction is normally accomplished at a temperaure of 0° to 150° C. instantaneously or within 12 hours.

The common starting material, i.e. the compound (II), in the above procedures is readily prepared by the method as described in J. Med. Chem., 26, 97 (1983).

Some typical examples for preparation of the aniline derivatives (I) are illustratively shown below.

EXAMPLE 1

Preparation of isopropyl N-(3,5-dichloro-4-methoxymethylphenyl)carbamate according to Procedure (a):

3,5-Dichloro-4-methoxymethylaniline (2.06 g) and N,N-diethylaniline (1.49 g) were dissolved in toluene (15 ml). To the resultant solution was dropwise added isopropyl chloroformate (1.24 g) in 5 minutes under ice-cooling. The resultant mixture was allowed to stand at room temperature for 12 hours, poured into ice-water and extracted with ethyl acetate. The extract was washed with water, dried over magnesium sulfate and concentrated under reduced pressure. The residue was purified by silica gel chromatography using a mixture of toluene and ethyl acetate as the eluent to give isopropyl N-(3,5-dichloro-4-methoxymethylphenyl)carbamate (Compound No. 1) (2.62 g) in a yield of 89.6% $n_D^{26.2}$ 1.5283.

NMR δ (CDCl$_3$): 7.31 (s, 2H), 6.83 (broad, 1H), 4.95 (m, 1H), 4.60 (s, 2H), 3.38 (s, 3H), 1.27 (d, 6H).

EXAMPLE 2

Preparation of 1-methyl-2-propynyl N-(3,5-dimethyl-4-propionylphenyl)carbamate according to Procedure (b):

3,5-Dimethyl-4-propionylaniline (1.77 g) in toluene (20 ml) was dropwise added to a toluene solution containing 10 g of phosgene at 10° to 20° C. The resulting mixture was gradually heated and, after being refluxed for 30 minutes, cooled to room temperature. The solvent was removed by distillation uner reduced pressure to give crude 3,5-dimethyl-4-propionylphenyl isocyanate. The thus obtained crude substance was added to a toluene solution (50 ml) containing triethylamine (1.0 g) and 1-butyn-3-ol (0.75 g). The resultant mixture was allowed to stand at room temperature for 12 hours, poured into ice-water and extracted with ethyl acetate. The extract was washed with water, dried over magnesium sulfate and concentrated under reduced pressure. The residue was purified by silica gel chromatography using a mixture of toluene and ethyl acetate as the eluent to give 1-methyl-2-propynyl N-(3,5-dimethyl-4-propionylphenyl)carbamate (Compound No. 60) (2.45 g) in a yield of 89.9%. $n_D^{23.0}$ 1.5247.

EXAMPLE 3

Preparation of isopropyl N-methyl-N-(3,5-dimethyl-4-propionylphenyl)carbamate according to Procedure (c):

Isopropyl N-(3,5-dimethyl-4-propionylphenyl)carbamate (2.63 g) and iodomethane (4.30 g) were dissolved in tetrahydrofuran (10 ml). The resultant solution was dropwise added to a solution containing potassium hydroxide (1.68 g) and tetra-n-butylammonium bromide (1.0 g). After being allowed to stand at room temperature for 12 hours, the reaction mixture was poured into ice-water and extracted with toluene. The extract was washed with water, dried over magnesiunm sulfate and concentrated under reduced pressure. The residue was purified by silica gel chromatography using a mixture of toluene and ethyl acetate as the eluent to give isopropyl N-methyl-N-(3,5-dimethyl-4-propionylphenyl)carbamate (Compound No. 40) (2.60 g) in a yield of 93.8%. $n_D^{20.0}$ 1.5120.

Specific examples of the aniline derivatives (I) of the invention, which can be readily prepared according to Procedure (a), (b) or (c), are shown in Table 1.

TABLE 1

Structure:

$$\underset{R}{\underset{|}{\overset{X\phantom{XXXX}Y}{\text{Ar}}}}-N(Z)-\overset{A}{\underset{\|}{C}}-B$$

(Phenyl ring with X, Y at meta positions, R at para, and N(Z)-C(=A)-B at the other meta/substituent position)

| Compound No. | X | Y | R | Z | A | B | Physical constant |
|---|---|---|---|---|---|---|---|
| 1 | —Cl | —Cl | —CH$_2$OCH$_3$ | —H | O | —O(i)Pr | $n_D^{26.2}$ 1.5283 |
| 2 | —H | —OC$_2$H$_5$ | —CH$_2$CH=CH$_2$ | —H | O | —O(i)Pr | $n_D^{23.0}$ 1.5188 |
| 3 | —H | —OC$_2$H$_5$ | —CH$_2$CH$_2$CH$_3$ | —H | O | —O(i)Pr | $n_D^{21.0}$ 1.5121 |
| 4 | —H | —OCH$_3$ | —COOCH$_3$ | —H | O | —O(i)Pr | M.P. 90.5–92° C. |
| 5 | —Cl | —OC$_2$H$_5$ | —C(=O)—C$_2$H$_5$ | —H | O | —O(i)Pr | |
| 6 | —Cl | —OC$_2$H$_5$ | —CH$_2$CH$_2$CH$_3$ | —H | O | —O(i)Pr | |
| 7 | —Cl | —CH$_2$OCH$_3$ | —C(=O)—C$_2$H$_5$ | —H | O | —O(i)Pr | |
| 8 | —CH$_3$ | —OC$_2$H$_5$ | —C(=O)—C$_2$H$_5$ | —H | O | —O(i)Pr | M.P. 85–86° C. |
| 9 | —CH$_3$ | —OC$_2$H$_5$ | —CH$_2$CH$_2$CH$_3$ | —H | O | —O(i)Pr | |
| 10 | —OCH$_3$ | —OCH$_3$ | —SO$_2$NH$_2$ | —H | O | —O(i)Pr | |
| 11 | —NO$_2$ | —COOCH$_3$ | —CH$_2$OCH$_3$ | —H | O | —O(i)Pr | |
| 12 | —CH$_3$ | —CH$_3$ | —C(=O)—C$_2$H$_5$ | —H | O | —O(i)Pr | $n_D^{23.0}$ 1.5179 |
| 13 | —CH$_3$ | —CH$_2$CH$_2$CH$_3$ | —C(=O)—C$_2$H$_5$ | —H | O | —O(i)Pr | M.P. 181–183° C. |
| 14 | —Cl | —NH—C(=O)—OCH$_3$ | —NH—C(=O)—CH$_3$ | —H | O | —O(i)Pr | M.P. 133–134° C. |
| 15 | —H | —OC$_2$H$_5$ | —NH—C(=O)—OCH$_3$ | —H | O | —O(i)Pr | Oily substance |
| 16 | —CH$_3$ | —CH$_3$ | —I | —H | O | —O(i)Pr | |
| 17 | —CH$_3$ | —CH$_3$ | —C≡CH | —H | O | —O(i)Pr | |
| 18 | —CH$_3$ | —CH$_3$ | —CH$_2$Cl | —H | O | —O(i)Pr | |
| 19 | —CH$_3$ | —CH$_3$ | —CH$_2$OCH$_3$ | —H | O | —O(i)Pr | |

TABLE 1-continued

| Compound No. | X | Y | R | Z | A | B | Physical constant |
|---|---|---|---|---|---|---|---|
| 20 | —CH₃ | —CH₃ | —C≡N | —H | O | —O(i)Pr | |
| 21 | —CH₃ | —CH₃ | —CH₂CN | —H | O | —O(i)Pr | |
| 22 | —CH₃ | —CH₃ | —CH₂SCH₃ | —H | O | —O(i)Pr | |
| 23 | —CH₃ | —CH₃ | —C(=O)—H | —H | O | —O(i)Pr | |
| 24 | —CH₃ | —CH₃ | —C(=O)—OCH₃ | —H | O | —O(i)Pr | |
| 25 | —CH₃ | —CH₃ | —CH=NOCH₃ | —H | O | —O(i)Pr | |
| 26 | —CH₃ | —CH₃ | —C(=O)—NH₂ | —H | O | —O(i)Pr | |
| 27 | —CH₃ | —CH₃ | —N=CHCH₃ | —H | O | —O(i)Pr | |
| 28 | —CH₃ | —CH₃ | —NHC₂H₅ | —H | O | —O(i)Pr | |
| 29 | —CH₃ | —CH₃ | —NH—C(=O)—SCH₃ | —H | O | —O(i)Pr | |
| 30 | —CH₃ | —CH₃ | —NH—C(=O)—NHCH₃ | —H | O | —O(i)Pr | |
| 31 | —CH₃ | —CH₃ | —SC₂H₅ | —H | O | —O(i)Pr | |
| 32 | —CH₃ | —CH₃ | —SOC₂H₅ | —H | O | —O(i)Pr | |
| 33 | —CH₃ | —CH₃ | —SO₂C₂H₅ | —H | O | —O(i)Pr | |
| 34 | —CH₃ | —CH₃ | —SO₂OCH₃ | —H | O | —O(i)Pr | |
| 35 | —CH₃ | —CH₃ | —SO₂NHC₂H₅ | —H | O | —O(i)Pr | |
| 36 | —CH₃ | —CH₃ | —SO₂N(CH₃)₂ | —H | O | —O(i)Pr | |
| 37 | —CH₃ | —CH₃ | —SO₂NHCH₂CH=CH₂ | —H | O | —O(i)Pr | |
| 38 | —CH₃ | —CH₃ | —SO₂NHCH₂C≡CH | —H | O | —O(i)Pr | $n_D^{22.5}$ 1.5437 |
| 39 | —H | —OC₂H₅ | —NHCOOCH₃ | —OH | O | —O(i)Pr | $n_D^{22.5}$ 1.5482 |
| 40 | —CH₃ | —CH₃ | —C(=O)—C₂H₅ | —CH₃ | O | —O(i)Pr | $n_D^{20.0}$ 1.5120 |

TABLE 1-continued
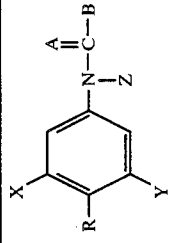
| Compound No. | X | Y | R | Z | A | B | Physical constant |
|---|---|---|---|---|---|---|---|
| 41 | —CH₃ | —CH₃ | —C(=O)—C₂H₅ | —CH₂CH=CH₂ | O | —O(i)Pr | |
| 42 | —CH₃ | —CH₃ | —C(=O)—C₂H₅ | —CH₂C≡CH | O | —O(i)Pr | |
| 43 | —CH₃ | —CH₃ | —C(=O)—C₂H₅ | —CH(CH₃)—COOCH₃ | O | —O(i)Pr | |
| 44 | —CH₃ | —CH₃ | —C(=O)—C₂H₅ | —C(=O)—CH₃ | O | —O(i)Pr | |
| 45 | —CH₃ | —CH₃ | —C(=O)—C₂H₅ | —C(=O)—cyclopropyl | O | —O(i)Pr | |
| 46 | —CH₃ | —CH₃ | —C(=O)—C₂H₅ | —C(=O)—C₆H₅ | O | —O(i)Pr | |
| 47 | —CH₃ | —CH₃ | —C(=O)—C₂H₅ | —SCH₃ | O | —O(i)Pr | |
| 48 | —CH₃ | —CH₃ | —C(=O)—C₂H₅ | —S—C₆H₅ | O | —O(i)Pr | |
| 49 | —CH₃ | —CH₃ | —C(=O)—C₂H₅ | —SCOOC₂H₅ | O | —O(i)Pr | |

TABLE 1-continued

| Compound No. | X | Y | R | Z | A | B | Physical constant |
|---|---|---|---|---|---|---|---|
| 50 | —CH$_3$ | —CH$_3$ | —C(=O)—C$_2$H$_5$ | —H | O | —OCH$_3$ | n$_D^{20.5}$ 1.5383 |
| 51 | —CH$_3$ | —CH$_3$ | —C(=O)—C$_2$H$_5$ | —H | O | —OC$_2$H$_5$ | n$_D^{20.5}$ 1.5310 |
| 52 | —CH$_3$ | —CH$_3$ | —C(=O)—C$_2$H$_5$ | —H | S | —O(i)Pr | |
| 53 | —CH$_3$ | —CH$_3$ | —C(=O)—C$_2$H$_5$ | —H | O | —(i)Pr | M.P. 137–138° C. |
| 54 | —CH$_3$ | —CH$_3$ | —C(=O)—C$_2$H$_5$ | —H | O | —CH=CHCH$_3$ | n$_D^{22.7}$ 1.5540 |
| 55 | —CH$_3$ | —CH$_3$ | —C(=O)—C$_2$H$_5$ | —H | O | cyclopropyl | M.P. 149–150° C. |
| 56 | —CH$_3$ | —CH$_3$ | —C(=O)—C$_2$H$_5$ | —H | O | phenyl | M.P. 133–134° C. |
| 57 | —CH$_3$ | —CH$_3$ | —C(=O)—C$_2$H$_5$ | —H | O | —SC$_2$H$_5$ | n$_D^{20.0}$ 1.5595 |
| 58 | —CH$_3$ | —CH$_3$ | —C(=O)—C$_2$H$_5$ | —H | O | 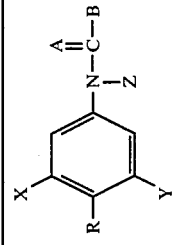 | |

TABLE 1-continued

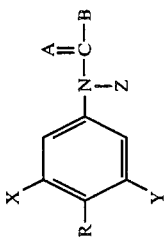

| Compound No. | X | Y | R | Z | A | B | Physical constant |
|---|---|---|---|---|---|---|---|
| 59 | $-CH_3$ | $-CH_3$ | $-\underset{\underset{O}{\parallel}}{C}-C_2H_5$ | $-H$ | O | $-O-CH-CH=CH_2$<br>$\quad\quad\quad\mid$<br>$\quad\quad\quad CH_3$ | $n_D^{23.0}$ 1.5254 |
| 60 | $-CH_3$ | $-CH_3$ | $-\underset{\underset{O}{\parallel}}{C}-C_2H_5$ | $-H$ | O | $-O-CH-C\equiv CH$<br>$\quad\quad\quad\mid$<br>$\quad\quad\quad CH_3$ | $n_D^{23.0}$ 1.5247 |
| 61 | $-CH_3$ | $-CH_3$ | $-\underset{\underset{O}{\parallel}}{C}-C_2H_5$ | $-H$ | O | $-OCH_2CH=CHCH_2Cl$ | $n_D^{22.7}$ 1.5310 |
| 62 | $-CH_3$ | $-CH_3$ | $-\underset{\underset{O}{\parallel}}{C}-C_2H_5$ | $-H$ | O | $-OCH_2C\equiv CCH_2Cl$ | $n_D^{22.7}$ 1.5423 |
| 63 | $-CH_3$ | $-CH_3$ | $-\underset{\underset{O}{\parallel}}{C}-C_2H_5$ | $-H$ | O | $-OCH\!\!-\!\!\!\triangle$<br>$\quad\mid$<br>$\quad CH_3$ | $n_D^{23.0}$ 1.5210 |
| 64 | $-CH_3$ | $-CH_3$ | $-\underset{\underset{O}{\parallel}}{C}-C_2H_5$ | $-H$ | O | $-OCH(CH_2Br)_2$ | $n_D^{23.0}$ 1.5430 |
| 65 | $-CH_3$ | $-CH_3$ | $-\underset{\underset{O}{\parallel}}{C}-C_2H_5$ | $-H$ | O | $-OCH_2CF_3$ | M.P. 66–68° C. |
| 66 | $-CH_3$ | $-CH_3$ | $-\underset{\underset{O}{\parallel}}{C}-C_2H_5$ | $-H$ | O | $\quad\quad CH_2Cl$<br>$\quad\quad\mid$<br>$-OCH$<br>$\quad\quad\mid$<br>$\quad\quad CH_2OCH_3$ | $n_D^{22.7}$ 1.5211 |
| 67 | $-CH_3$ | $-CH_3$ | $-\underset{\underset{O}{\parallel}}{C}-C_2H_5$ | $-H$ | O | $-OCH_2CH_2CN$ | M.P. 83–85° C. |

TABLE 1-continued

[Structure: benzene ring with X, Y at meta positions, R at para, and N(Z)-C(=A)-B group]

| Compound No. | X | Y | R | Z | A | B | Physical constant |
|---|---|---|---|---|---|---|---|
| 68 | —CH$_3$ | —CH$_3$ | —C(=O)—C$_2$H$_5$ | —H | O | —OCH(CH$_2$OCH$_3$)CH$_3$ | $n_D^{20.0}$ 1.5161 |
| 69 | —CH$_3$ | —CH$_3$ | —C(=O)—C$_2$H$_5$ | —H | O | —OCH(CH$_3$)—C$_6$H$_5$ | $n_D^{23.0}$ 1.5569 |
| 70 | —CH$_3$ | —CH$_3$ | —C(=O)—C$_2$H$_5$ | —H | O | —OCH$_2$CH$_2$OCH$_2$CH=CH$_2$ | |
| 71 | —CH$_3$ | —CH$_3$ | —C(=O)—C$_2$H$_5$ | —H | O | —OCH$_2$CH$_2$OCH$_2$CH$_2$Cl | |
| 72 | —CH$_3$ | —CH$_3$ | —C(=O)—C$_2$H$_5$ | —H | O | —O—CH(CH$_3$)—O—C$_6$H$_5$ | |
| 73 | —CH$_3$ | —CH$_3$ | —C(=O)—C$_2$H$_5$ | —H | O | —OCH$_2$CH$_2$OCH$_2$—C$_6$H$_5$ | |
| 74 | —CH$_3$ | —CH$_3$ | —C(=O)—CH$_3$ | —H | O | —O(i)Pr | $n_D^{21.0}$ 1.5306 |
| 75 | —CH$_3$ | —CH$_3$ | —C(=O)—C$_3$H$_7$ | —H | O | —O(i)Pr | |

TABLE 1-continued structure:
$$\begin{array}{c} X \\ \phantom{X} \\ \phantom{X}\text{-}\overset{A}{\underset{\|}{C}}\text{-}B \\ \text{N-Z} \end{array}$$
(phenyl ring with X, R, Y substituents; N-Z attached to ring; N bonded to C(=A)-B)

| Compound No. | X | Y | R | Z | A | B | Physical constant |
|---|---|---|---|---|---|---|---|
| 76 | —CH₃ | —CH₃ | —C(=O)—CH₂Br | —H | O | —OCH₃ | M.P. 72–75° C. |
| 77 | —CH₃ | —CH₃ | —C(=O)—CH₂Br | —H | O | —O(i)Pr | $n_D^{22.0}$ 1.5472 |
| 78 | —H | —OC₂H₅ | —C(=O)—C₂H₅ | —H | O | —OCH₃ | $n_D^{19.5}$ 1.5424 |
| 79 | —H | —OC₂H₅ | —C(=O)—C₂H₅ | —H | O | —O(i)Pr | M.P. 53–55° C. |
| 80 | —CH₃ | —CH₃ | —SO₂NH₂ | —H | O | —O(i)Pr | M.P. 134–137.5° C. |
| 81 | —Cl | —NHCOOCH₃ | —CH₂CH₂CH₃ | —H | O | —O(i)Pr | |
| 82 | —CH₃ | —CH₃ | —C(=O)—(cyclopropyl) | —H | O | —O(i)Pr | $n_D^{22.5}$ 1.5344 |
| 83 | —CH₃ | —CH₃ | —C(=O)—C₂H₅ | —H | O | —O-(2-fluorophenyl) | Oily substance |
| 84 | —CH₃ | —CH₃ | —C(=NOH)—CH₃ | —H | O | —O(i)Pr | |

In the practical use of the aniline derivatives of the formula (I) as fungicides, they may be applied as such or in a formulation form such as dusts, wettable powders, oil sprays, emulsifiable concentrates, tablets, granules, fine granules, aerosols or flowables. Such formulation form can be formulated in a conventional manner by mixing at least one of the compounds (I) with an appropriate solid or liquid carrier(s) or diluent(s) and, if necessary, an appropriate adjuvant(s) (e.g. surfactants, adherents, dispersants, stabilizers) for improving the dispersibility and other properties of the active ingredient.

Examples of the solid carriers or diluents are botanical materials (e.g. flour, tobacco stalk powder, soybean powder, walnut-shell powder, vegetable powder, saw dust, bran, bark powder, cellulose powder, vegetable extract residue), fibrous materials (e.g. paper, corrugated cardboard, old rags), synthetic plastic powders, clays (e.g. kaolin, bentonite, fuller's earth), talcs, other inorganic materials (e.g. pyrophyllite, sericite, pumice, sulfur powder, active carbon) and chemical fertilizers (e.g. ammonium sulfate, ammonium phosphate, ammonium nitrate, urea, ammonium chloride).

Examples of the liquid carriers or diluents are water, alcohols (e.g. methanol, ethanol), ketones (e.g. acetone, methylethylketone), ethers (e.g. diethyl ether, dioxane, cellosolve, tetrahydrofuran), aromatic hydrocarbons (e.g. benzene, toluene, xylene, methyl naphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, carbon tetrachloride), etc.

Examples of the surfactants are alkyl sulfuric esters, alkyl sulfonates, alkylaryl sulfonates, polyethylene glycol ethers, polyhydric alcohol esters, etc. Examples of the adherents and dispersants may include casein, gelatin, starch powder, carboxymethyl cellulose, gum arabic, alginic acid, lignin, bentonite, molasses, polyvinyl alcohol, pine oil and agar. As the stabilizers, there may be used PAP (isopropyl acid phosphate mixture), tricresyl phosphate (TCP), tolu oil, epoxydized oil, various surfactants, verious fatty acids and their esters, etc.

The foregoing formulations generally contain at least one of the aniline derivatives of the formula (I) in a concentration of about 1 to 95% by weight, preferably of 2.0 to 80% by weight. By using the formulations, the compounds (I) are generally applied in such amounts as 2 to 100 g per 10 are.

When only the drug-resistant strains of phytopathogenic fungi are present, the compounds (I) may be used alone. However, when the drug-sensitive strains are present together with the drug-resistant strains, their alternate use with benzimidazole, thiophanate fungicides and/or cyclic imide fungicides or their combined use with benzimidazole, thiophanate fungicides and/or cyclic imide fungicides is favorable. In such alternate or combined use, each active ingredient may be employed as such or in conventional agricultural composition forms. In case of the combined use, the weight proportion of the compound of the formula (I) and the benzimidazole, thiophanate fungicide and/or the cyclic imide fungicide may be from about 1:0.1 to 1:10.0.

Typical examples of the benzimidazole thiophanate fungicides and the cyclic imide fungicides are shown in Table 2.

TABLE 2

| Compound | Structure | Name |
|---|---|---|
| A | benzimidazole with —NHCOOCH$_3$ and N-CONHC$_4$H$_9$(n) | Methyl 1-(butylcarbamoyl)benzimidazol-2-yl-carbamate |
| B | benzimidazole with 4-thiazolyl group, NH | 2-(4-Thiazolyl)benzimidazole |
| C | benzimidazole with —NHCOOCH$_3$, NH | Methyl benzimidazol-2-ylcarbamate |
| D | benzimidazole with 2-furyl group, NH | 2-(2-Furyl)benzimidazole |
| E | benzene with two ortho —NHCNHCOOCH$_3$ (C=S) groups | 1,2-Bis(3-methoxycarbonyl-2-thioureido)benzene |

TABLE 2-continued

| Compound | Structure | Name |
|---|---|---|
| F | (benzene with two ortho NHC(S)NHCOOC$_2$H$_5$ groups) | 1,2-Bis(3-ethoxycarbonyl-2-thioureido)benzene |
| G | (benzene with NHC(S)NHCOOCH$_3$ and ortho NHP(=O)(SCH$_3$)(OCH$_3$)) | 2-(O,S—Dimethylphosphorylamino)-1-(3'-methoxycarbonyl-2'-thioureido)benzene |
| H | (benzene with NHC(S)NHCOOCH$_3$ and ortho NHP(=S)(OCH$_3$)(OCH$_3$)) | 2-(O,O—Dimethylthiophosphorylamino)-1-(3'-methoxycarbonyl-2'-thioureido)benzene |
| I | (3,5-dichlorophenyl attached to N of 1,2-dimethylcyclopropane-1,2-dicarboximide) | N—(3',5'-Dichlorophenyl)-1,2-dimethylcyclopropane-1,2-dicarboximide |
| J | (3,5-dichlorophenyl-imidazolidine-2,4-dione with N—C(=O)—NHCH(CH$_3$)$_2$) | 3-(3',5'-Dichlorophenyl)-1-isopropylcarbamoylimidazolidine-2,4-doine |
| K | (3,5-dichlorophenyl oxazolidine-2,4-dione with CH=CH$_2$ and CH$_3$) | 3-(3', 5'-Dichlorophenyl)-5-methyl-5-vinyloxazolidine-2,4-dione |
| L | (3,5-dichlorophenyl oxazolidine-2,4-dione with COOC$_2$H$_5$ and CH$_3$) | Ethyl (RS)—3-(3',5'-dichlorophenyl)-5-methyl-2,4-dioxo-oxazolidine-5-carboxylate |

Besides, the aniline derivatives of the formula (I) may be also used in admixture with other fungicides, herbicides, insecticides, miticides, fertilizers, etc.

When the compounds (I) are used as fungicides, they may be applied in such amounts as 2 to 100 grams per 10 ares. However, this amount may vary depending upon composition forms, application times, application methods, application sites, diseases, crops and so on, and therefore, they are not limited to particular amounts.

Some practical embodiments of the fungicidal composition according to the present invention are illustratively shown in the following Examples wherein % and part(s) are by weight.

FORMULATION EXAMPLE 1

Two parts of Compound No. 1, 88 parts of clay and 10 parts of talc are thoroughly pulverized and mixed together to obtain a dust formulation containing 2% of the active ingredient.

FORMULATION EXAMPLE 2

Thirty parts of Compound No. 12, 45 parts of diatomaceous earth, 20 parts of white carbon, 3 parts of sodium laurylsulfate as a wetting agent and 2 parts of calcium ligninsulfonate as a dispersing agent are mixed while being powdered to obtain a wettable powder formulation containing 30% of the active ingredient.

FORMULATION EXAMPLE 3

Fifty parts of Compound No. 50, 45 parts of diatomaceous earth, 2.5 parts of calcium alkylbenzenesulgonate as a wetting agent and 2.5 parts of calcium ligninsulfonate as a dispersing agent are mixed while being powdered to obtain a wettable powder formulation containing 50% of the active ingredient.

FORMULATION EXAMPLE 4

Ten parts of Compound No. 51, 80 parts of cyclohexanone and 10 parts of polyoxyethylene alkylaryl ether as an emulsifier are mixed together to obtain an emulsifiable concentrate formulation containing 10% of the active ingredient.

FORMULATION EXAMPLE 5

One part of Compound No. 77, 1 part of Compound I, 88 parts of clay and 10 parts of talc are thoroughly pulverized and mixed together to obtain a dust formulation containing 2% of the active ingredient.

FORMULATION EXAMPLE 6

Twenty parts of Compound No. 57, 10 parts of Compound J, 45 parts of diatomaceous earth, 20 parts of white carbon, 3 parts of sodium laurylsulfate as a wetting agent and 2 parts of calcium ligninsulfonate as a dispersing agent are mixed while being powdered to obtain a wettable powder formulation containing 30% of the active ingredient.

FORMULATION EXAMPLE 7

Ten parts of Compound No. 68, 40 parts of Compound A, 45 parts of diatomaceous earth, 2.5 parts of calcium alkylbenzenesulfonate as a wetting agent and 2.5 parts of calcium ligninsulfonate as a dispersing agent are mixed while being powdered to obtain a wettable powder formulation containing 50% of the active ingredient.

Typical test data indicating the excellent fungicidal activity of the compounds (I) are shown below. The compounds used for comparison are as follows:

| Compound | Remarks |
|---|---|
| Swep 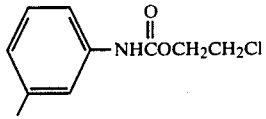 | Commercially available herbicide |
| Chlorpropham 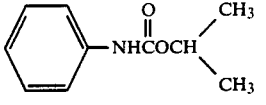 | Commercially available herbicide |
| Barban 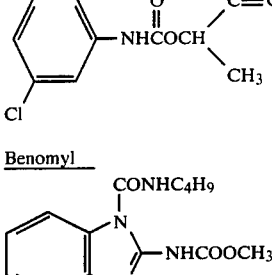 | Commercially available herbicide |
| CEPC 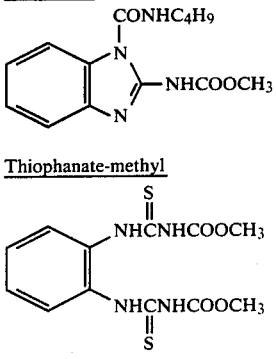 | Commercially available herbicide |
| Propham 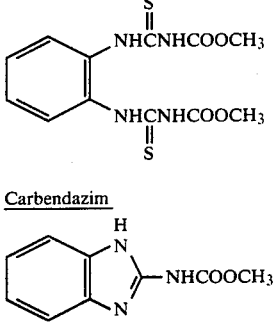 | Commercially available herbicide |
| Chlorobufam 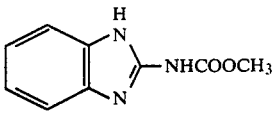 | Commercially available herbicide |
| Benomyl | Commercially available fungicide |
| Thiophanate-methyl | Commercially available fungicide |
| Carbendazim | Commercially available fungicide |

EXPERIMENT 1

Protective activity test on powdery mildew of cucumber (Sphaerotheca fuliginea):

A flower pot of 90 ml volume was filed with sandy soil, and seeds of cucumber (var: Sagami-hanjiro) were sowed therein. Cultivation was carried out in a greenhouse for 8 days. Onto the resulting seedlings having cotyledons, the test compound formulated in emulsifiable concentrate or wettable powder and diluted with water was sprayed at a rate of 10 ml per pot. Then, the seedlings were inoculated with a spore suspension of the drug-resistant or drug-sensitive strain of Sphaerotheca fuliginea by spraying and further cultivated in the greenhouse. Ten days thereafter, the infectious state of the plants was observed. The degree of damage was determined in the following manner, and the results are shown in Table 3.

The leaves examined were measured for a percentage of infected area and classified into the corresponding disease indices, 0, 0.5 1, 2, 4:

| Disease index | Percentage of infected area |
| --- | --- |
| 0 | No infection |
| 0.5 | Infected area of less than 5% |
| 1 | Infected area of less than 20% |
| 2 | Infected area of less than 50% |
| 4 | Infected area of not less than 50% |

The disease severity was calculated according to the following equation:

$$\text{Disease severity (\%)} = \frac{\Sigma\{(\text{Disease index}) \times (\text{Number of leaves})\}}{4 \times (\text{Total number of leaves examined})} \times 100$$

The prevention value was calculated according to the following equation:

$$\text{Prevention value (\%)} = 100 - \frac{(\text{Disease severity in treated plot})}{(\text{Disease severity in untreated plot})} \times 100$$

TABLE 3

| Compound No. | Concentration of active ingredient (ppm) | Prevention value when inoculated with drug-resistant strain (%) | Prevention value when inoculated with drug-sensitive strain (%) |
| --- | --- | --- | --- |
| 1 | 500 | 100 | 0 |
| 12 | 500 | 100 | 0 |
| 50 | 500 | 100 | 0 |
| 51 | 500 | 100 | 0 |
| 57 | 500 | 100 | 0 |
| 68 | 500 | 100 | 0 |
| Swep | 200 | 0 | 0 |
| Chlorpropham | 200 | 0 | 0 |
| Barban | 200 | 25 | 0 |
| CEPC | 200 | 0 | 0 |
| Propham | 200 | 0 | 0 |
| Chlorbufam | 200 | 0 | 0 |
| Benomyl | 200 | 0 | 100 |
| Thiophanate-methyl | 200 | 0 | 100 |
| Carbendazim | 200 | 0 | 100 |

As understood from the results shown in Table 3, the compounds of the formula (I) of the present invention exhibit an excellent preventive effect on the drug-resistant strain but do not exhibit any preventive effect on the tested drug-sensitive strain. To the contrary, commercially available known fungicides such as Benomyl, Thiophanate-methyl and Carbendazim show a notable controlling effect on the drug-sensitive strain but not on the drug-resistant strain. Other tested compounds structurally similar to the compounds of the formula (I) do not show any fungicidal activity on the drug-sensitive strain and the drug-resistant strain.

EXPERIMENT 2

Preventive effect on cercospora leaf spot of sugarbeet (*Cercospora beticola*):

A flower pot of 90 ml volume was filled with sandy soil, and seeds of sugarbeet (var: Detroit dark red) were sowed therein. Cultivation was carried out in a greenhouse for 20 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Cercospora beticola* by spraying. The pot was covered with a polyvinyl chloride sheet to make a condition of high humidity, and cultivation was continued in the greenhouse for 10 days. The degree of damage was determined in the same manner as in Experiment 1, and the results are shown in Table 4.

TABLE 4

| Compound No. | Concentration of active ingredient (ppm) | Prevention value when inoculated with drug-resistant strain (%) | Prevention value when inoculated with drug-sensitive strain (%) |
| --- | --- | --- | --- |
| 51 | 500 | 100 | 0 |
| 57 | 500 | 100 | 0 |
| 68 | 500 | 100 | 0 |
| Swep | 200 | 0 | 0 |
| Chlorpropham | 200 | 0 | 0 |
| Barban | 200 | 34 | 0 |
| CEPC | 200 | 0 | 0 |
| Propham | 200 | 0 | 0 |
| Chlorbufam | 200 | 0 | 0 |
| Benomyl | 200 | 0 | 100 |
| Thiophanate-methyl | 200 | 0 | 100 |
| Carbendazim | 200 | 0 | 100 |

As understood from the results shown in Table 4, the compounds of the formula (I) of the invention exhibit an excellent preventive effect on the drug-resistant strain but do not exhibit any preventive effect on the tested drug-sensitive strain. To the contrary, commecially available known fungicides such as Benomyl and Thiophanate-methyl exhibit a notable controlling effect on the drug-sensitive strain but not on the drug-resistant strain. Other tested compounds structurally similar to the compounds of the formula (I) do not exhibit any fungicidal activity on the drug-sensitive strain and the drug-resistant strain.

EXPERIMENT 3

Preventive effect on scab of pear (*Venturia nashicola*):

A plastic pot of 90 ml volume was filled with sandy soil, and seeds of pear (var: Chojuro) were sowed therein. Cultivation was carried out in a greenhouse for 20 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Venturia nashicola* by spraying. The resulting plants were placed at 20° C. under a condition of high humidity for 3 days and then at 20° C. under irradiation with a fluorescent lamp for 20 days. The degree of damage was determined in the same manner as in Experiment 1, and the results are shown in Table 5.

TABLE 5

| Compound No. | Concentration of active ingredient (ppm) | Prevention value when inoculated with drug-resistant strain (%) | Prevention value when inoculated with drug-sensitive strain (%) |
| --- | --- | --- | --- |
| 12 | 500 | 100 | 0 |
| 50 | 500 | 100 | 0 |
| 51 | 500 | 100 | 0 |
| Benomyl | 200 | 0 | 100 |
| Thiophanate-methyl | 200 | 0 | 100 |

As understood from the results shown in Table 5, the compounds of the formula (I) of the invention exhibit an excellent preventive effect on the drug-resistant strain but do not exhibit any preventive effect on the tested drug-sensitive strain. To the contrary, commercially available known fungicides such as Benomyl and Thiophanate-methyl exhibit a notable controlling effect on the drug-sensitive strain but not on the drug-resistant strain.

EXPERIMENT 4

Preventive effect on brown leaf-spot of peanut (*Cercospora arachidicola*):

Plastic pots of 90 ml volume was filled with sandy soil, and seeds of peanut (var: Chiba hanryusei) were sowed therein. Cultivation was carried out in a greenhouse for 14 days. Onto the resulting seedlings, the test compound formulated in emulsifiable concentrate or wettable powder and diluted with water was sprayed at a rate of 10 ml per pot. Then, the seedlings were inoculated with a spore suspension of the dsug-resistant or drug-sensitive strain of *Cercospora arachidicola* by spraying. The resulting plants were covered with a polyvinyl chloride sheet to make a condition of humidity and cultivated in the greenhouse for 10 days. The degree of damage was determined in the same manner as in Experimant 1, and the results are shown in Table 6.

TABLE 6

| Compound No. | Concentration of active ingredient (ppm) | Prevention value when inoculated with drug-resistant strain (%) | Prevention value when inoculated with drug-sensitive strain (%) |
| --- | --- | --- | --- |
| 12 | 500 | 100 | 0 |
| 50 | 500 | 100 | 0 |
| 51 | 500 | 100 | 0 |
| Benomyl | 200 | 0 | 100 |
| Thiophanate-methyl | 200 | 0 | 100 |

As understood from the results shown in Table 6, the compounds of the formula (I) of the present invention exhibit an excellent preventive effect on the drug-resistant strain but do not exhibit any preventive effect on the tested drug-sensitive strain. To the contrary, commercially available known fungicides such as Benomyl and Thiophanate-methyl exhibit a notable controlling effect on the drug-sensitive strain but not on the drug-resistant strain.

EXPERIMENT 5

Preventive effect on gray mold of cucumber (*Botrytis cinerea*):

A plastic pot of 90 ml volume is filled with sandy soil, and seeds of cucumber (var: Sagami-hanjiro) are sowed therein. Cultivation was carried out in a greenhouse for 8 days to obtain cucumber seedlings expanding cotyledons. Onto the resulting seedlings, the test compound formulated in emulsifiable concentrate or wettable powder and diluted with water were sprayed at a rate of 10 ml per pot. After air-drying, the seedlings were inoculated with mycelial disks (5 mm in diameter) of the drug-resistant or drug-sensitive strain of *Botrytis cinerea* by putting them on the leaf surfaces. After the plants are infected by incubating under high humidity at 20° C. for 3 days, the rates of disease severity are observed. The degree of damage is determined in the same manner as in Experiment 1, and the results are shown in Table 7.

TABLE 7

| Compound No. | Concentration of active ingredient (ppm) | Prevention value when inoculated with drug-resistant strain (%) | Prevention value when inoculated with drug-sensitive strain (%) |
| --- | --- | --- | --- |
| 1 | 500 | 100 | 0 |
| 12 | 500 | 100 | 0 |
| 50 | 500 | 100 | 0 |
| 51 | 500 | 100 | 0 |
| 57 | 500 | 100 | 0 |
| 68 | 500 | 100 | 0 |
| Benomyl | 200 | 0 | 100 |
| Thiophanate-methyl | 200 | 0 | 100 |

As understood from the results shown in Table 7, the compounds (I) of the present invention exhibit an excellent preventive effect on the drug-resistant strain but do not exhibit any preventive effect on the tested drug-sensitive strain. To the contrary, commercially available known fungicides such as Benomyl and Thiophanate-methyl exhibit a notable controlling effect on the drug-sensitive strain but not on the drug-resistant strain.

EXPERIMENT 6

Preventive effect on gummy stem blight of cucumber (*Mycosphaerella melonis*):

A plastic pot of 90 ml volume is filled with sandy soil, and seeds of cucumber (var: Sagami-hanjiro) are sowed therein. Cultivation was carried out in a greenhouse for 8 days to obtain cucumber seedlings exponding cotyledons. Onto the resulting seedlings, the test compound formulated in emulsifiable concentrate or wettable powder and diluted with water was sprayed at a rate of 10 ml per pot. After air-drying, the seedlings were inoculated with mycelial disks (5 mm in diameter) of the drug-resistant or drug-sensitive strain of *Mycosphaerella melonis* by putting them on the leaf surfaces. After the plants were infected by incubating under high humidity at 25° C. for 4 days, the rates of disease severity were observed. The degree of damage was determined in the same manner as in Experiment 1, and the results are shown in Table 8.

TABLE 8

| Compound No. | Concentration of active ingredient (ppm) | Prevention value when inoculated with drug-resistant strain (%) | Prevention value when inoculated with drug-sensitive strain (%) |
| --- | --- | --- | --- |
| 12 | 500 | 100 | 0 |
| 68 | 500 | 100 | 0 |
| Benomyl | 200 | 0 | 100 |
| Thiophanate-methyl | 200 | 0 | 100 |

As understood from the results shown in Table 8, the compounds of the formula (I) of the present invention exhibit an excellent preventive effect on the drug-resistant strain but do not exhibit any preventive effect on the tested drug-sensitive strain. To the contrary, commercially known fungicides such as Benomyl and Thiophanate-methyl exhibit a notable controlling effect on the drug-sensitive strain but not on the drug-resistant strain.

EXPERIMENT 7

Preventive effect on green mold of orange (*Penicillium italicum*):

Fruits of orange (var: Unshu) were washed with water and dried in the air. The fruits were immersed in a solution of the test compound prepared by diluting an emulsifiable concentrate comprising the test compound with water for 1 minute. After drying in the air, the fruits were inoculated with a spore suspension of the drug-resistant or drug-sensitive strain of *Penicillium italicum* by spraying and placed in a room of high humidity for 14 days. The degree of damage was determined in the following manner.

The fruits examined were measured for a percentage of infected area and classified into the corresponding indices, 0, 1, 2, 3, 4, 5:

| Disease index | Percentage of infected area |
| --- | --- |
| 0 | No infection |
| 1 | Infected area of less than 20% |
| 2 | Infected area of less than 40% |
| 3 | Infected area of less than 60% |
| 4 | Infected area of less than 80% |
| 5 | Infected area of not less than 80% |

Calculation of the degree of damage and the prevention value was made as in Experiment 1.

The results are shown in Table 9.

TABLE 9

| Compound No. | Concentration of active ingredient (ppm) | Prevention value when inoculated with drug-resistant strain (%) | Prevention value when inoculated with drug-sensitive strain (%) |
| --- | --- | --- | --- |
| 12 | 500 | 100 | 0 |
| 51 | 500 | 100 | 0 |
| 57 | 500 | 100 | 0 |
| Benomyl | 200 | 0 | 100 |
| Thiophanate-methyl | 200 | 0 | 100 |

As understood from the results shown in Table 9, the compounds of the formula (I) of the present invention exhibit an excellent preventive effect on the drug-resistant strain but do not exhibit any preventive effect on the tested drug-sensitive strain. To the contrary, commercially available known fungicides such as Benomyl and Thiophanate-methyl exhibit a notable controlling effect on the drug-sensitive strain but not on the drug-resistant strain.

EXPERIMENT 8

Phytotoxicity on crop plants:

Plastic pots of 150 ml volume were filled with sandy soil, and seeds of wheat (var: Norin No. 61), apple (var: Kogyoku) and peanut (var: Chiba hanryusei) were sowed therein. Cultivation was carried out in a greenhouse. Onto the resulting seedlings, the test compound formulated in emulsifiable concentrate or wettable powder and diluted with water was sprayed. After cultivation in the greenhouse for additional 10 days, the phytotoxicity was examined on the following criteria:

| Extent | Observation |
| --- | --- |
| − | No abnormality |
| + | Abnormality due to phytotoxicity observed in a part of crop plants |
| ++ | Abnormality due to phytotoxicity observed in entire crop plants |
| +++ | Crop plants withered due to phytotoxicity |

The results are shown in Table 10.

TABLE 10

| Compound No. | Concentration of active ingredient (ppm) | Phytotoxicity Wheat | Apple | Peanut |
| --- | --- | --- | --- | --- |
| 2 | 1000 | − | − | − |
| 12 | 1000 | − | − | − |
| 50 | 1000 | − | − | − |
| Barban | 1000 | − | ++ | ++ |
| CEPC | 1000 | − | ++ | ++ |
| Swep | 1000 | ++ | ++ | + |

As understood from the results shown in Table 10, the compounds of the formula (I) of the present invention produce no material phytotoxicity, while commercially available herbicides having a chemical structure similar thereto produce considerable phytotoxicity.

EXPERIMENT 9

Preventive effect on powdery mildew of cucumber (*Spaerotheca fuliginea*):

A plastic pot of 90 ml volume was filled with sandy soil, and seeds of cucumber (var: Sagami-hanjiro) were sowed therein. Cultivation was carried out in a greenhouse for 8 days. Onto the resulting seedlings having cotyledons, the test compound(s) formulated in emulsifiable concentrate or wettable powder and diluted with water were sprayed at a rate of 10 ml per pot. Then, the seedlings were inoculated with a mixed spore suspension of the drug-resistant and drug-sensitive strain of *Sphaerotheca fuliginea* by spraying and further cultivated in the greenhouse. Ten days thereafter, the infectious state of the plants was observed. The degree of damage was determined in the same manner as in Experiment 1, and the results are shown in Table 11.

TABLE 11

| Compound No. | Concentration of active ingredient (ppm) | Prevention value (%) |
| --- | --- | --- |
| 1 | 100 | 38 |
| 1 | 20 | 0 |
| 12 | 100 | 40 |
| 12 | 20 | 0 |
| 50 | 100 | 42 |
| 50 | 20 | 0 |
| A | 100 | 45 |
| A | 20 | 12 |
| B | 500 | 42 |
| B | 100 | 10 |
| C | 100 | 42 |
| C | 20 | 8 |
| D | 500 | 36 |
| D | 100 | 0 |
| E | 100 | 44 |
| E | 20 | 10 |
| F | 100 | 43 |
| F | 20 | 8 |
| G | 100 | 42 |
| G | 20 | 8 |
| H | 100 | 40 |
| H | 20 | 5 |
| 1 + A | 20 + 20 | 100 |

TABLE 11-continued

| Compound No. | Concentration of active ingredient (ppm) | Prevention value (%) |
|---|---|---|
| 1 + B | 20 + 20 | 100 |
| 1 + E | 20 + 20 | 100 |
| 1 + G | 20 + 20 | 100 |
| 12 + C | 20 + 20 | 100 |
| 12 + D | 20 + 20 | 100 |
| 12 + F | 20 + 20 | 100 |
| 12 + H | 20 + 20 | 100 |
| 50 + A | 20 + 20 | 100 |
| 50 + D | 20 + 20 | 100 |
| 50 + E | 20 + 20 | 100 |
| 50 + G | 20 + 20 | 100 |

As understood from the results shown in Table 11, the combined use of the compounds of the formula (I) of the present invention with benzimidazole, thiophanate fungicides and/or cyclic imide fungicides exhibit a much more excellent preventive effect than their sole use.

EXPERIMENT 10

Preventive effect on gray mold of tomato (*Botrytis cinerea*):

A plastic pot of 90 ml volume was filled with sandy soil, and seeds of tomato (var: Fukuji No. 2) were sowed therein. Cultivation was carried out in a greenhouse for 4 weeks. Onto the resulting seedlings at the 4-leaf stage, the test compound(s) formulated in emulsifiable concentrate or wettable powder and diluted with water were sprayed at a rate of 10 ml per pot. Then, the seedlings were inoculated with a mixed spore suspension of the drug-resistant and drug-sensitive strain of *Botrytis cinerea* by spraying and placed at 20° C. in a room of high humidity for 5 days. The degree of damage was determined in the same manner as in Experiment 1, and the results are shown in Table 12.

TABLE 12

| Compound No. | Concentration of active ingredient (ppm) | Prevention value (%) |
|---|---|---|
| 51 | 100 | 42 |
| 51 | 20 | 0 |
| 57 | 100 | 40 |
| 57 | 20 | 0 |
| 68 | 100 | 38 |
| 68 | 20 | 0 |
| I | 100 | 48 |
| I | 20 | 22 |
| J | 500 | 46 |
| J | 100 | 18 |
| K | 100 | 42 |
| K | 20 | 15 |
| L | 500 | 42 |
| L | 100 | 12 |
| 51 + I | 20 + 50 | 100 |
| 51 + J | 20 + 50 | 100 |
| 57 + I | 20 + 50 | 100 |
| 57 + K | 20 + 50 | 100 |
| 68 + I | 20 + 50 | 100 |
| 68 + J | 20 + 50 | 100 |
| 68 + K | 20 + 50 | 100 |
| 68 + L | 20 + 50 | 100 |

As understood from the results shown in Table 12, the combined use of the compounds of the formula (I) of the present invention with benzimidazole, thiophanate fungicides and/or cyclic imide fungicides exhibit a much more excellent preventive effect than their sole use.

What is claimed is:

1. A compound of the formula:

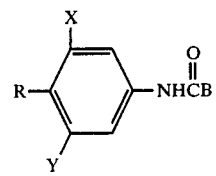

wherein X is a lower alkyl group; Y is a lower alkyl or lower alkoxy group; R is a lower alkanoyl group; and B is a lower alkoxy group.

2. A fungicidal composition which comprises as an essential active ingredient a fungicidally effective amount of a compound according to claim 1.

3. A method for controlling plant pathogenic fungi which comprises applying a fungicidally effective amount of at least one compound according to claim 1 to said plant pathogenic fungi.

4. A compound according to claim 1, which is:

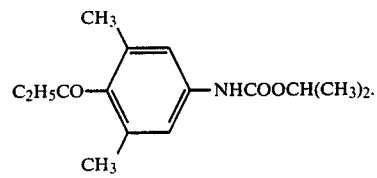

5. The compound according to claim 1, which is represented by the formula:

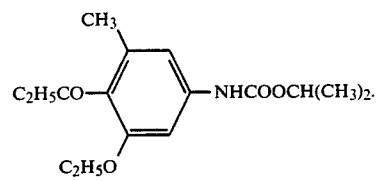

6. A method for controlling plant pathogenic fungi which comprises applying a fungicidally effective amount of the compound of claim 5 to plant pathogenic fungi.

7. A fungicidal composition comprising as an essential active ingredient a fungicidally effective amount of the compound of claim 5 and an inert carrier or diluent.

8. The fungicidal composition according to claim 7, which further comprises as an additional active ingredient(s) at least one benzimidazole and thiophanate fungicides and/or cyclic imide fungicides.

* * * * *